United States Patent
Danylewych-May et al.

(10) Patent No.: US 6,291,821 B1
(45) Date of Patent: Sep. 18, 2001

(54) METHOD OF MONITORING THE STATUS OF THE GAS DRYING SYSTEM IN AN ION MOBILITY SPECTROMETER

(75) Inventors: Ludmila Danylewych-May, North York; Frank Kuja, Brampton, both of (CA)

(73) Assignee: Barringer Research Limited, Mississauga (CA)

( * ) Notice: Subject to any disclaimer, the term of this patent is extended or adjusted under 35 U.S.C. 154(b) by 0 days.

(21) Appl. No.: 09/453,075

(22) Filed: Dec. 2, 1999

(51) Int. Cl.[7] .............................. B01D 59/44; H01J 49/00
(52) U.S. Cl. .............................................. 250/286
(58) Field of Search ........................ 250/286; 436/52, 436/103, 153

(56) References Cited

U.S. PATENT DOCUMENTS

| | | | |
|---|---|---|---|
| 5,071,771 | * 12/1991 | Barbour et al. | 436/153 |
| 5,405,781 | * 4/1995 | Davies et al. | 436/52 |
| 5,457,316 | * 10/1995 | Cohen et al. | 250/286 |
| 5,510,268 | * 4/1996 | Doring et al. | 436/103 |
| 5,796,099 | * 8/1998 | Jackson | 250/286 |

* cited by examiner

Primary Examiner—Jack Berman
Assistant Examiner—Johnnie L Smith
(74) Attorney, Agent, or Firm—Bereskin & Parr

(57) ABSTRACT

A method is provided for monitoring the concentration of water vapor in an ion mobility spectrometer which measures the drift time of a selected ion, having a tendency to form clusters of water molecules. As these clusters are formed, the drift time of the ion varies, and by monitoring this variation in drift time, a measure of the concentration of water vapor can be made. If this exceeds a certain level, a warning can be given and/or the instrument disabled. Preferably, a comparison is made between two different ions, one having at least a moderate tendency to form clusters with water molecules, and the other having a weak tendency to form such clusters. By comparing the two drift times, a relatively accurate determination of water concentration can be made, and this can automatically allow for variations of drift times due to other causes.

11 Claims, 3 Drawing Sheets

METHOD OF MONITORING THE STATUS OF THE GAS DRYING SYSTEM IN AN ION MOBILITY SPECTROMETER

FIELD OF THE INVENTION

This invention relates to Ion Mobility Spectrometers (IMS), a class of chemical or mass analyzers used to identify trace constituents of a gas mixture by ionizing them, introducing a number of the resulting ions into a space to which an electric field is applied, and measuring the time taken for the ions to traverse the length of this drift space under the influence of the field. It particularly relates to the monitoring of the water vapour concentration in the air or gas supplied to an IMS, and the provision of advance warning to the operator of the need to service the air-drying sub-system of the instrument.

BACKGROUND OF THE INVENTION

Ion Mobility Spectrometers (IMS) identify trace constituents of a gas mixture by ionizing them, introducing a number of the resulting ions into a space to which an electric field is applied, and measuring the time taken for the ions to traverse the length of this drift space under the influence of the field. At the end of the drift space, the ions strike a collector electrode and produce current pulses, and the time history of the collector current, showing a series of pulses corresponding to the arrival of ions of different types, is known as a plasmagram. The length of time, $t_d$, for an ion to traverse the drift space and reach the collector electrode is known as its drift time, and depends on the size and mass of the ion and the charge it carries, on the length of the drift space, and on the field strength, temperature and gas pressure therein. To a first approximation, this dependence can be described by the relation $$t_d = (1/K_0) * (L/E) * (273.5/T) * P/760 \tag{1}$$

where T is the gas temperature (degrees Kelvin), P is the pressure (Torr), L is the length of the drift space, E is the electric field (assumed uniform over L), and $K_0$, commonly called the reduced mobility, is a constant characteristic of the particular ion. Because of the statistical nature of the collision process, and the existence of a radial component to the electric field, there will actually be a narrow range of drift times for each species of ion. That is, even if all the ions of a given species enter the drift space simultaneously, they will reach the collector at different times, and produce a current pulse of finite width. In a practical instrument, the plasmagram peak is the convolution of this pulse with the shape of the voltage pulse used to gate ions from the ionization region into the drift region. The widths of the plasmagram peaks set a limit to the resolution of the IMS, that is, the ability to distinguish between ions with similar values of $K_0$.

The operation of an IMS is strongly affected, in many ways, by the presence of water vapour in the gas in the ionization and drift regions. In particular, neutral water molecules will form clusters with many types of analyte ion, with the number of water molecules clustered with each ion depending on the nature of the ion, the gas temperature, and the concentration of water molecules. These clusters are larger than the original ion, and thus have lower values of $K_0$. Clusters may grow or shrink during their drift time, and thus exhibit $K_0$ values intermediate between those for clusters with integer numbers of water molecules. The net effect is that, if the concentration of water increases, the drift time for a ion which forms clusters will increase and the peak will widen, which may cause the ion to be miss-classified, or to overlap and hide another peak. For this reason, most IMS instruments continuously purge the ionization and drift spaces with a gas flow which has been carefully dried to a water content of a few parts in $10^5$. This is an extremely low level of water vapour, and an operator needs to know if the drying system is not meeting the permissable maximum humidity level. Accordingly, there is a need for a device and method to monitor the performance of the drying system. This is especially true for instruments where the drift gas is atmospheric air dried by a consumable desiccant. Even with scheduled preventive maintenance, and the use of indicating desiccants, many factors, ranging from operator inattention to unusually high ambient humidity, may result in the IMS being operated under non-optimum conditions, with consequent loss of sensitivity and increase in false-alarm rate. Also, the humidity levels involved are below the range of conventional commercial moisture sensors.

The prior art proposes several solutions to the problem of instability in the IMS drift times of certain species due to variable formation of clusters with water. U.S. Pat. No. 5,405,781 teaches the use of a filter to remove water from the gas circulated through the IMS, and also the advisability, in IMS systems which use calibrants to compensate for temperature and like variables, of selecting, as calibrants, materials which have a minimal tendency to form clusters with water. U.S. Pat. No. 5,405,781 teaches the use of a supplementary thermal gas drying system to prolong the useful life of an absorption filter in an IMS. However, neither this patent nor other prior art reveal any means of monitoring the water vapour concentration in an IMS so as to be assured that it is within acceptable limits for the application.

SUMMARY OF THE INVENTION

The present invention is based on the realization that it is possible to make use of the change in drift time(s) of one or more known ion species to monitor the water concentration in an IMS and to generate a warning when this concentration approaches an undesirable level. The species used are ones which are deliberately injected, or are always present because they are normal atmospheric constituents.

It is a premise of the invention that certain ions will always be present in an IMS, in easily detectable amounts, either because they arise from normal constituents of atmospheric air, or because they are deliberately injected, and, further, that some of these ions will readily form clusters with water. As a result, their apparent drift times will increase, in a predictable, and easily detectable, manner, if the water vapour concentration in the IMS increases. The invention monitors the absolute drift time of one, or the difference in drift times of two of these species, and, when the measured time increases above a preset alarm value, issues an alert to the operator. The alarm value is chosen to correspond to a level of water vapour concentration below that which will cause unacceptable degradation in system performance.

BRIEF DESCRIPTION OF THE DRAWING FIGURES

For a better understanding of the present invention and to show more clearly how it may be carried into effect, reference will now be made, by way of example, to the accompanying drawings, in which.

DETAILED DESCRIPTION OF THE PREFERRED EMBODIMENTS

Figure 1:
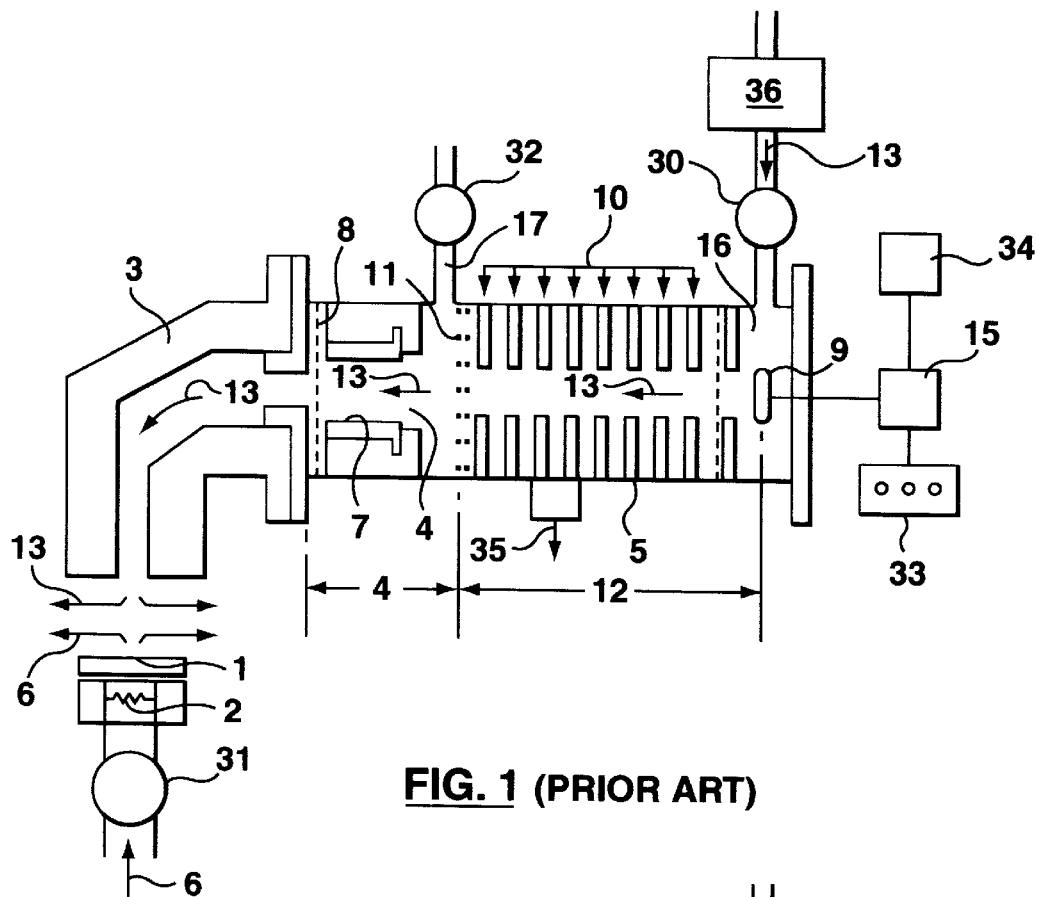
FIGS. 1 and 2 are schematic views of an ion mobility spectrometer in accordance with a known prior art design.
Figure 2:
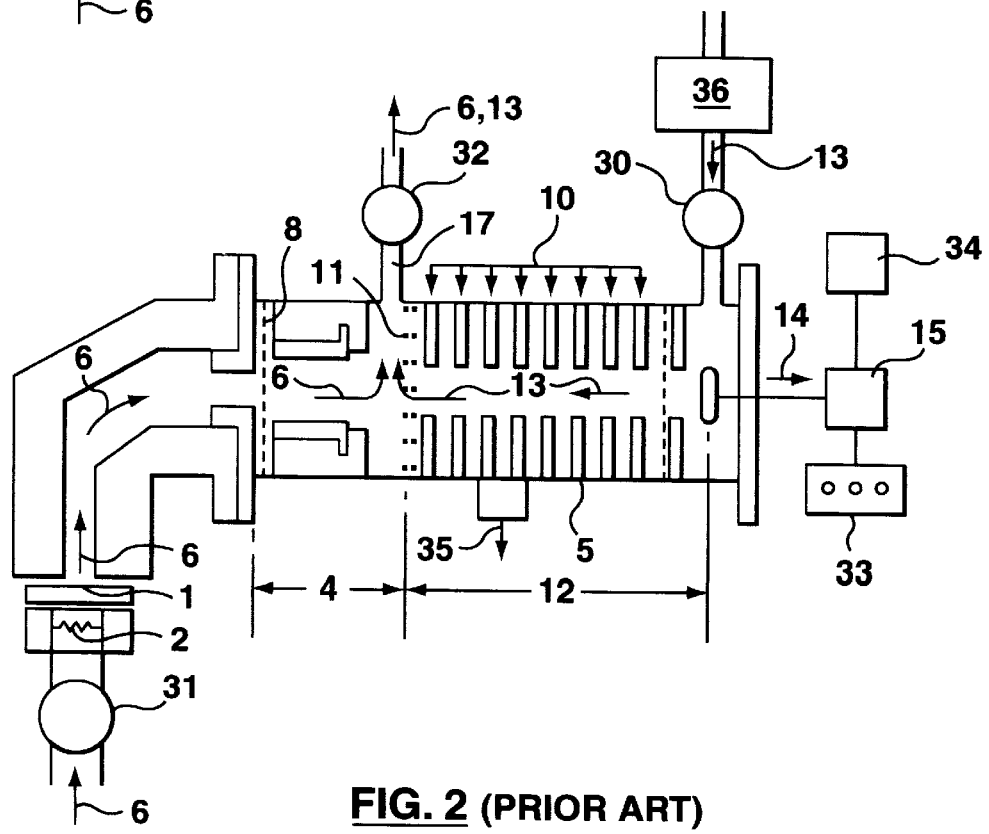

The present invention is applicable to any suitable ion mobility spectrometer. U.S. Pat. No. 5,796,099 describes in detail a typical IMS, and the contents thereof are hereby incorporated by reference; FIGS. 1 and 2 show an ion mobility spectrometer as in this U.S. patent.

The IMS system of U.S. Pat. No. 5,796,099 incorporates internal calibrant features, and relies on a transition from a calibration (or READY) mode to a sample testing (or ANALYSIS) mode. In this case, the sample 1 consists of particles or a condensed phase from which vapours are liberated by application of heat from a desorber heater 2, with the vapours carried through a heated sample gas inlet passageway 3 to the ionization/reaction region 4 of an IMS drift tube 5 by a flow of sample carrier gas 6. Alternatively, samples already in the vapour state may be introduced in a similar fashion or by injection through a septum.

Vapours in the ionization/reaction region 4 are ionized by electrons emitted from an electron source 7 such as $^{63}$Ni, and by interactions with other vapour molecules present, which may include added reactants. It will be understood that any suitable ionization source can be provided. An electric field gradient is established between a repelling ring 8 at the entrance to the drift tube and a collector electrode 9 at the other end of the drift tube through the use of drift rings 10 in a drift region 12. Ions of appropriate polarity move to the electronic gating grid 11, which separates the ionization/reaction region 4 and the drift region 12 of the drift tube 5. Ions are gated out of the ionization/reaction in known manner. For example, the grating grid can comprise a pair of fine meshes, spaced about 1 mm apart that enable a packet of ions to be discharged into the drift region 12. The packet of ions can have a short axial extent, to give good resolution.

Progress of ions to the drift region is stopped by a small opposite potential at the gating grid 11. This gating grid potential is periodically reversed for short periods of time, typically 200 microseconds, during which interval a packet of ions enters the drift region 12 and moves toward the collector electrode 9 against a counterflow of drift gas 13. During this movement, the different ionic species in the package separate, with the smaller, lighter ions reaching the collector electrode 9 ahead of larger heavier ions. If the electric field in the drift region 12 is such that negatively charged ions reach the collector 9, the IMS is said to operate in the negative mode. If the electric field is such that positive ions reach the collector, the IMS is said to operate in the positive mode.

Figure 4:
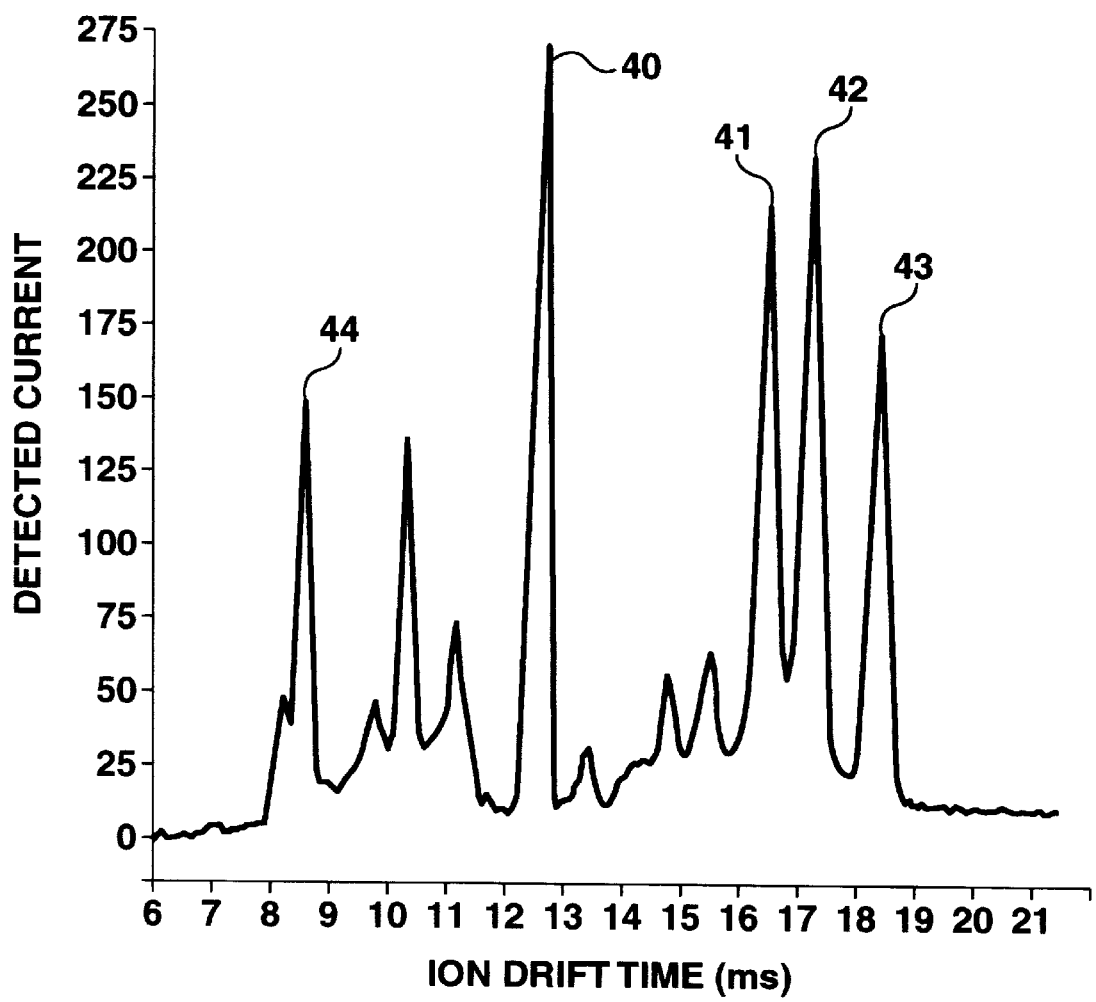
FIG. 4 is a graph showing the variation of detected current with ion drift time.

The current produced at the collector electrode 9 by the arrival of such ions is measured as a function of the time elapsed from the last gating pulse. This time is called drift time. FIG. 4 is a graphic representation of an exemplary measurement of collector current as a function of drift time (a "plasmagram"). Each of the peaks in the figure corresponds to the arrival at the collector of ions of a particular type. Typically, gating pulses are repeated every 30 milliseconds. The collector current signals 14 are digitized in a controller system 15, with multiple scans being added together to form one analysis sample reading, typically consisting of about 20 scans. Several analysis sample readings are obtained throughout the sample desorption period of typically 5 to 10 seconds.

The controller system 15 is connected to a display 33. In known manner, the controller system can include conventional elements for control by a computer, e.g. memory, a central processor and a data storage facility.

The flow of drift gas 13 enters the drift tube 5 at the collector electrode end 16. In the new inventive arrangement, the flow 13 contains small amounts of calibrant(s) and tracer(s). A calibrant is a material which products a strong plasmagram peak under all operating conditions and has a weak tendency to cluster with water vapour. A tracer is a material which will produce a strong plasmagram peak under all operating conditions and has a moderate to strong tendency to cluster with water vapour. In the preferred embodiment of the invention, nicotinamide is used as calibrant and hydronium ion ($H_3O^+$) as tracer in positive mode, and in negative mode, the calibrant is 4-nitrobenzonitrile and the tracer is the negative ion of molecular oxygen ($O_2-$). Both tracers are present in normal atmospheric air and do not have to be added.

This flow is maintained in both READY and ANALYSIS modes by valve 30. The sample carrier gas flow 6 only enters the inlet 3 and drift tube 5 through valve 31 in the ANALYSIS mode. The exhaust suction flow through the exhaust port 17 is only activated by valve 32 in the ANALYSIS mode. In the READY mode, the sample carrier gas flow 6 disperses into the air surrounding the desorber 2, and the exhaust port 17 is closed. Thus, in the ANALYSIS mode, both flows 6 and 13 are exhausted through the exhaust port 17; the arrows in FIG. 1 indicate the READY mode and in FIG. 2 the ANALYSIS mode.

In known manner, the drift gas flow 13, supplied to a valve 13, is air from a source 36, which commonly is a device for drying atmospheric air. With time, the effectiveness of the source 36 degrades, and it is this degradation that is monitored by the present invention. Also, it is conventional not to dry air supplied as carrier gas 6. For small hand held units, to reduce the drying requirements, air exiting from valve 32 can be recycled to the source 36.

In READY mode, the drift gas containing trace amounts of calibrant(s) and tracer(s) therefore passes through the drift tube 5. The calibrant and tracer molecules in the drift gas are ionized in the ionization/reaction region 4 and repelled towards the gating grid 11, where activation of the gating pulse will allow a packet of ions including the ionized calibrant(s) and tracer(s) to move into the drift region 12 towards the collector electrode 9.

Figure 3:
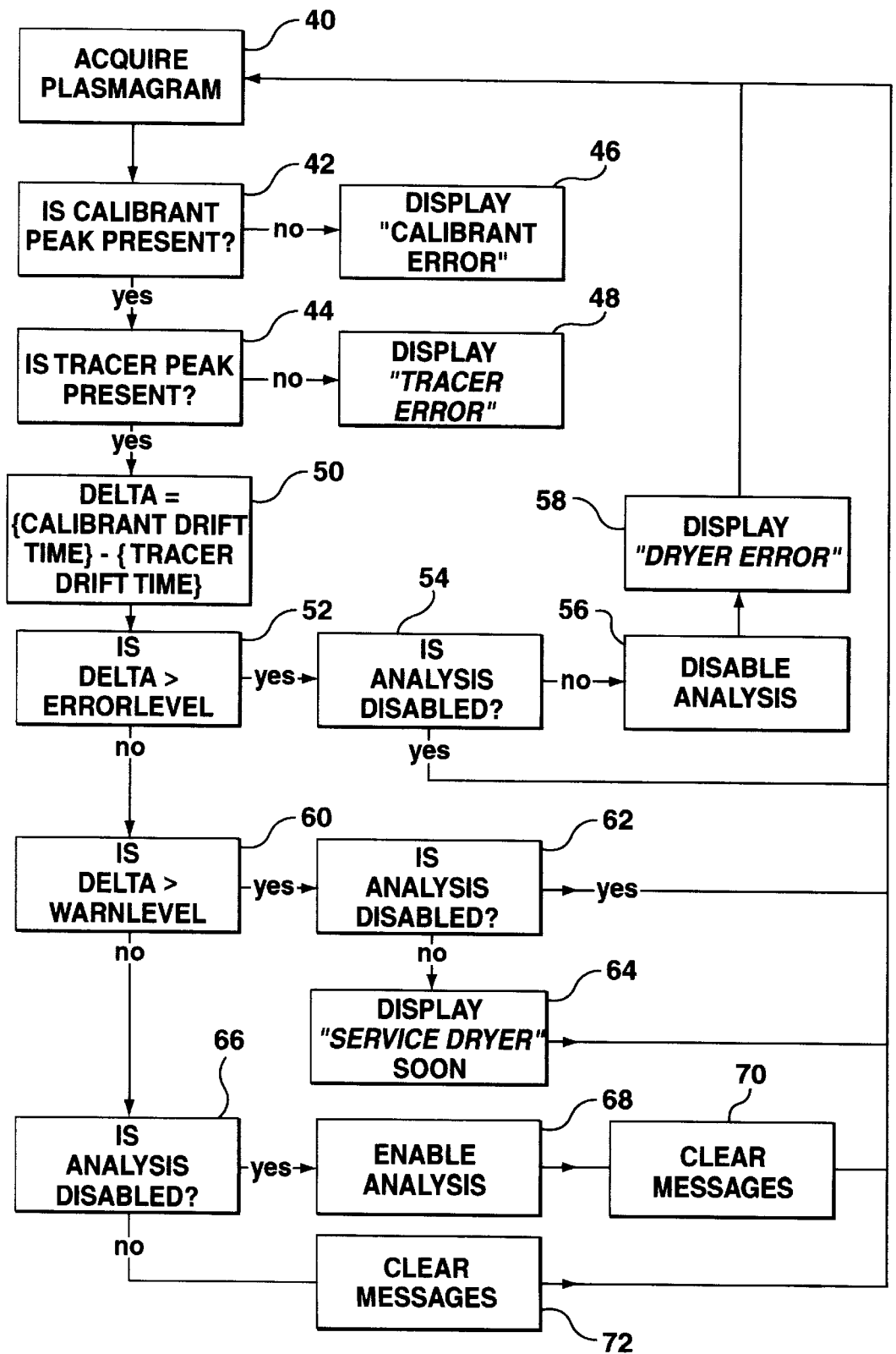
FIG. 3 is a block diagram of the logic used to control automatic implementation of the preferred embodiment of the method.

Once the drift tube temperature, as measured by a sensor 35, reaches a preset value, calibrant and tracer ions are regularly pulsed into the drift region 12. The calibrant and tracer peaks are identified by searching in predetermined permissible drift time windows in the plasmagram, and the calibrant and tracer drift times are recorded, as indicated at 40, ACQUIRE PLASMAGRAM (FIG. 3). The dryer monitor software routine first determines that the calibrant and tracer peaks are present at adequate signal-to-noise ratios, as indicated at 42 and 44; if they are not present, then as indicated at 46 and 48 an error signal is given. The routine then compares the measured time interval between these peaks (DELTA) to a first preset level (ERRORLEVEL), as indicated at 50. If DELTA is greater than ERRORLEVEL, shown at 52, the routine disables the IMS from going into ANALYSIS mode at 54 and 56, and alerts the operator, via an error message on the display 33 (FIGS. 1 and 2) and indicated at 58 (FIG. 3), that the dryer system is unserviceable. The routine then acquires a new plasmagram and checks the new value of DELTA, and continues in this loop until DELTA falls below ERRORLEVEL. If DELTA is less than ERRORLEVEL, the routine, at 60, then checks if DELTA is greater than a second, lower preset level (WARNINGLEVEL). If so, at 62, the routine first checks if ANALYSIS is disabled, and if it is, acquires a new plasmagram and repeats the test. If DELTA is greater than WARNINGLEVEL, and ANALYSIS is not inhibited, the routine displays a warning on the display 33 (FIGS. 1 and 2) that the dryer system is in need of maintenance, as indicated at 64 in FIG. 3. If DELTA is less than WARNINGLEVEL the routine checks at 66 to see if analysis is disabled. If analysis is disabled, then it is enabled at 68 and messages cleared at 70; if analysis is not disabled, messages are cleared at 72. In either case, the routine then loops back to the beginning and acquires a new plasmagram at 40.

The actual measured calibrant drift time will vary within the permissible calibrant drift time window in accordance with the pressure and temperature condition within the drift tube 5. This calibrant drift time is subsequently used to calculate the expected drift times of the various target sample ions which may be present during a subsequent ANALYSIS mode.

Since the drift tube 5 and inlet 3 are an open system in the READY mode, the pressure within the drift tube during the READY mode is at or nearly at ambient or atmospheric level. An absolute pressure transducer 34 measures this pressure and provides a corresponding pressure signal to the system controller 15.

In the ANALYSIS mode, depicted in FIG. 2, a sample 1 is placed on the desorber heater 2 at the entrance of the sample gas inlet, and the system is sealed to the entrance of the inlet passageway 3. Sample carrier gas 6 containing the thermally desorbed sample vapours flows into the ionization/reaction region 4 through the sample gas inlet 3 in a direction counter to that of the drift gas 13. At the same time, the exhaust port 17 is opened, and an externally applied suction draws the sample carrier gas 6, drift gas 13, and un-ionized sample gas 6 out by this means.

In this mode the controller 15 searches in predicted time domain detection windows for the presence or absence of detector current signals arising in the drift time intervals calculated for anticipated target ions. The predicted time domain detection windows are established by relying on the measured absolute pressure and the temperature condition values established from calibrant ion drift times measured during READY mode. The prior measurement of the calibrant ion drift time in the READY mode is thus used to established the anticipated target ion drift time detection or search windows for various anticipated target ions.

The current signal from the collector 9 is searched for peaks which meet preset criteria for shape and amplitude and occur within the drift time windows predicted for the target ions. When such a peak is found, the processor 15 provides an indication to the operator, via the display 33, that the corresponding ion has been detected.

A graphic representation of an exemplary detector signal in ANALYSIS mode with annotations interpreting the signals is shown in FIG. 3. The peak 40 is the signal created by the arrival of the calibrant ion. Peak 41 is a cluster ion of PETN (pentaerythritol tetranitrate, an explosive) and a chloride ion. Peak 42 is a duster of PETN and a nitrate ion, and Peak 43 is a cluster of PETN and an ion derived from human finger oil, respectively. Peak 44 is the ($O_2-$) ion which is used as a tracer in the negative mode. The other peaks appearing at drift times shorter than the calibrant are background signals. The ion drift times of these substances appears from the X axis scale.

The procedure by which the existing system identifies target ions is as follows. Upon system start-up the system searches the calibrant search window for the appearance of a peak, once the flow rates of sample, drift, and exhaust gas have been established, the high voltage is stable, and the temperature indicators are at preset start-up levels. A peak detected in the time domain search window that satisfies certain pre-programmed criteria such a height and shape is recognized as the detection of a collector current signal corresponding to the calibrant ion. The instrument enters into READY mode when the calibrant ion is found and remains in READY mode as long as the drift time for the calibrant is within a predetermined range. The measured drift time for this calibrant ion is thereafter used to adjust the search window location for anticipated target ions amongst the sample ions when in ANALYSIS mode.

If the efficiency of the drying system degrades, allowing the concentration of water vapour in the system to increase, the depicted peaks will shift to the right on the X-axis scale and become wider, eventually reaching a point where the peaks will be misidentified. The present invention measures the shift of the tracer peak 44 relative to the calibrant 40 and alerts the operator before the shifts become large enough to affect the performance of the IMS.

What is claimed is:

1. A method of monitoring the concentration of water vapour in an ion mobility spectrometer the method comprising:

(1) selecting at least one ion species having a tendency to form clusters with water molecules;

(2) periodically measuring the drift time of the selected ion; and (3) from the measured drift time of the selected ion, determining if the concentration of water vapour is sufficiently large to degrade the performance of the ion mobility spectrometer.

2. A method as claimed in claim 1, wherein the selected ion is chosen from one of the constituents of normal, atmospheric air.

3. A method as claimed in claim 1, wherein the selected ion is provided by a tracer gas, and the method comprises supplying the tracer gas to the ion mobility spectrometer.

4. A method as claimed in claim 1 which comprises selecting one, tracer ion species having a moderate to strong tendency to form clusters with water vapour molecules and another, calibrant ion species having a weak tendency to form clusters with water vapour molecules, and the method comprising monitoring the difference in the drift times of said tracer and said calibrant ion species, to determine if the concentration of water vapour in the ion mobility spectrometer is sufficiently large to degrade the performance of the ion mobility spectrometer.

5. A method as claimed in claim 2, which includes selecting molecular oxygen with a single negative charge as the selected ion species.

6. A method as claimed in claim 2, which includes selecting the hydronium ion ($H_3O^+$) with a single positive charge as the selected ion species.

7. A method as claimed in claim 4, which includes providing nitrobenzonitrile with a single negative charge as the calibrant ion species.

8. A method as claimed in claim 4, which includes providing nicotinamide with a single positive charge as the calibrant ion species.

9. A method as claimed in claim 1, 2 or 3, which includes providing a water vapour alarm or indication to a user, if the detected concentration of water vapour exceeds a predetermined maximum permitted level.

10. A system for monitoring the concentration of water vapour in an ion mobility spectrometer, the system comprising; means for detecting the presence of a peak of at least one ion species, and for providing an error message if the peak is not detected; means for measuring the drift time of the selected ion species and for determining a measure of the concentration of the water vapour from the measured drift time; and at least one of means for providing a warning if the concentration of water vapour exceeds a certain level and means for disabling the mass spectrometer and providing a warning indication if the concentration of water vapour exceeds an error level.

11. A system as claimed in claim 10, further including a controller system for monitoring the concentration of water vapour within the ion mobility spectrometer.

* * * * *